United States Patent [19]

Kehoe

[11] Patent Number: 5,354,846
[45] Date of Patent: Oct. 11, 1994

[54] STREPTOLYSIN O ANTIGEN DERIVATIVES, ITS PRODUCTION AND USES

[76] Inventor: Michael Kehoe, 14 Springhouse La., Ebchester, County Durham, England

[21] Appl. No.: 74,287

[22] Filed: Jun. 8, 1993

Related U.S. Application Data

[63] Continuation of Ser. No. 812,887, Dec. 26, 1991, abandoned, which is a continuation of Ser. No. 438,721, Nov. 17, 1989, abandoned.

[30] Foreign Application Priority Data

Nov. 18, 1988 [GB] United Kingdom ............... 8827038

[51] Int. Cl.$^5$ ................. C07K 15/04; C07K 3/18; C12Q 1/04
[52] U.S. Cl. ......................... 530/350; 530/806; 530/413; 530/387.1; 436/518; 436/522
[58] Field of Search ............ 530/350, 806, 413, 387.1; 436/518, 522; 435/69.3

[56] References Cited

U.S. PATENT DOCUMENTS 4,379,850  4/1983  Ricci .................................. 436/517
4,629,783 12/1986  Cosand ............................... 530/324

OTHER PUBLICATIONS

Pomgor, S. 1987. Methods in Enzymology 154:450–473.
Creighton, T. E. Protein: Structures and Molecular Principles. (W. H. Freeman and Company, New York, 1983), pp. 93–99.
Lerner, R. A. 1982. Nature 299:592–596.
Kehoe et al. 1987,. Infection and Immmunity 55(12): 3228–3232.
Kehoe et al. 1984. Infection and Immunity 43(3): 804–810.

Primary Examiner—Keith C. Furman
Attorney, Agent, or Firm—Jan P. Brunelle; Walter H. Dreger

[57] ABSTRACT

A non-toxic and non-cytolytic derivative of streptolysin O which retains at least one (preferably immunodominant) epitope is produced, and can be used especially in diagnostic tests for detecting of the presence of antibodies to *Streptococcus pyogenes* in a

```
  1         .         .         .         .         .        60
ATGGATGCACAAACACGCCGCCGCGAACGTCGCGCAGAGAAACAGGCTCAATGGAAAGCA
 1 M  D  A  Q  T  R  R  R  R  E  R  R  A  E  K  Q  A  Q  W  K  A
       LAMBDA N PROTEIN       ~ 99 ↓ 100~ SLO
 61         .         .         .         .         .       120
GCAAATCCCCTGTTGGTTGGGGTAAGCGCAAAACCAGTTAACCAATGGCATGATAATTAT
21 A  N  P  L  L  V  G  V  S  A  K  P  V  N  Q  W  H  D  N  Y
                              (234)
121         .         .         .         .         .       180
TCTGGTGGTAATACGCTTCCTGCCAGAACACAATATACTGAATCAATGGTATATTCTAAG
41 S  G  G  N  T  L  P  A  R  T  Q  Y  T  E  S  M  V  Y  S  K
   (241)
181         .         .         .         .         .       240
TCACAGATTGAAGCAGCTCTAAATGTTAATAGCAAAATCTTAGATGGTACTTTAGGCATT
61 S  Q  I  E  A  A  L  N  V  N  S  K  I  L  D  G  T  L  G  I
   (261)
241         .         .         .         .         .       300
GATTTCAAGTCGATTTCAAAAGGTGAAAAGAAGGTGATGATTGCAGCATACAAGCAAATT
81 D  F  K  S  I  S  K  G  E  K  K  V  M  I  A  A  Y  K  Q  I
   (281)
301         .         .         .         .         .       360
TTTTACACCGTATCAGCAAACCTTCCTAATAATCCTGCGGATGTGTTTGATAAATCAGTG
101 F  Y  T  V  S  A  N  L  P  N  N  P  A  D  V  F  D  K  S  V
   (301)
361         .         .         .         .         .       420
ACCTTTAAAGAGTTGCAACGAAAAGGTGTCAGCAATGAAGCTCCGCCACTCTTTGTGAGT
122 T  F  K  E  L  Q  R  K  G  V  S  N  E  A  P  P  L  F  V  S
   (321)
421         .         .         .         .         .       480
AACGTAGCCTATGGTCGAACTGTTTTTGTCAAACTAGAAACAAGTTCTAAAAGTAATGAT
141 N  V  A  Y  G  R  T  V  F  V  K  L  E  T  S  S  K  S  N  D
   (341)
481         .         .         .         .         .       540
GTTGAAGCGGCCTTTAGTGCAGCTCTAAAAGGAACAGATGTTAAAACTAATGGAAAATAC
161 V  E  A  A  F  S  A  A  L  K  G  T  D  V  K  T  N  G  K  Y
   (361)
541     ↓   .         .         .         .         .       600
TCTGATATCTTAGAAAATAGCTCATTTACAGCTGTCGTTTTAGGAGGAGATGCTGCAGAG
181 S  D  I  L  E  N  S  S  F  T  A  V  V  L  G  G  D  A  A  E
   (381)
601         .         .         .         .         .       660
CACAATAAGGTAGTCACAAAAGACTTTGATGTTATTAGAAACGTTATCAAAGACAATGCT
201 H  N  K  V  V  T  K  D  F  D  V  I  R  N  V  I  K  D  N  A
   (401)
661         .         .         .         .         .       720
ACCTTCAGTAGAAAAAACCCAGCTTATCCTATTTCATACACCAGTGTTTTCCTTAAAAAT
221 T  F  S  R  K  N  P  A  Y  P  I  S  Y  T  S  V  F  L  K  N
   (421)
```

Fig.1A.

```
721                .         .         .         .         .         780
   AATAAAATTGCGGGTGTCAATAACAGAACTGAATACGTTGAAACAACATCTACCGAGTAC
241 N  K  I  A  G  V  N  N  R  T  E  Y  V  E  T  T  S  T  E  Y
   (441)
    781                .         .         .         .         .         840
   ACTAGTGGAAAAATTAACCTGTCTCATCAAGGCGCGTATGTTGCTCAATATGAAATCCTT
261 T  S  G  K  I  N  L  S  H  Q  G  A  Y  V  A  Q  Y  E  I  L
   (461)
    841                .         .         .         .         .         900
   TGGGATGAAATCAATTATGATGACAAAGGAAAAGAAGTGATTACAAAACGACGTTGGGAT
281 W  D  E  I  N  Y  D  D  K  G  K  E  V  I  T  K  R  R  W  D
   (481)
    901                .         .         .         .         .         960
   AACAACTGGTATAGTAAGACATCACCATTTAGCACAGTTATCCCACTAGGAGCTAATTCA
301 N  N  W  Y  S  K  T  S  P  F  S  T  V  I  P  L  G  A  N  S
   (501)
    961                .         .         .         .         .        1020
   CGAAATATACGTATCATGGCTAGAGAGTGCACCGGCTTAGCTTGGGAATGGTGGCGAAAA
321 R  N  I  R  I  M  A  R  E  C  T  G  L  A  W  E  W  W  R  K
   (521)
   1021                .         .         .         .         .        1080
   GTGATCGACGAAAGAGATGTGAAACTGTCTAAAGAAATCAATGTCAACATCTCAGGATCA
341 V  I  D  E  R  D  V  K  L  S  K  E  I  N  V  N  I  S  G  S
   (541)
   1081                .         .         .         .         .
   ACCCTGAGCCCATATGGTTCGATTACTTATAAG TAGGACTGGTTCAAGAGGTTC
361 T  L  S  P  Y  G  S  I  T  Y  K  371
   (561)                            (571)
```

Fig.1B

STREPTOLYSIN O ANTIGEN DERIVATIVES, ITS PRODUCTION AND USES

This is a continuation, of application Ser. No. 07/812,887 filed Dec. 20, 91; which is a continuation of application Ser. No. 07/438,721, both now abandoned.

BACKGROUND OF THE INVENTION

This invention relates to streptolysin O (SLO) antigens and their use, especially in diagnostic tests. In particular the present invention relates to the identification, construction and production of non-cytolytic and non-toxic SLO derivatives retaining antigenic sites that can detect antibodies in serum samples. The invention also relates to use of these SLO derivatives in diagnostic tests based on specific binding properties, such as binding between an antigen and an antibody.

SLO is a toxic cytolytic protein produced by *Streptococcus pyogenes* (*S.pyogenes*) which causes a number of human diseases. During infection, the gene encoding SLO is expressed and SLO is secreted by *S. pyogenes*. The toxicity of SLO seems to be closely associated with its cytolytic activity.

The infected human host produces anti-SLO antibodies to antigenic sites on the SLO molecule. Thus diagnostic tests detecting these anti-SLO antibodies in human serum, can indicate (past or present) infection by *S.pyogenes*. The immunodiagnostic assays presently being used for detection of anti-SLO antibodies in human serum utilise impure active SLO protein. These assays generally comprise the following steps:

(a) Take serum sample from patient.
(b) Make serial dilutions of serum sample in a suitable buffer.
(c) For each test include a control containing buffer, but no serum.
(d) Add a standard quantity of active SLO to each dilution of serum and to the control.
(e) Incubate the mixtures for a standard time and at a standard temperature, to allow any anti-SLO antibodies in the mixtures to combine with, and neutralise the added SLO.
(f) Add a standard quantity of red blood cells to each mixture.
(g) Incubate the mixtures for a standard time and at a standard temperature to allow any active (non-neutralised) SLO to lyse the added cells.
(h) Determine the highest dilution of serum that has neutralised the added SLO, that is which corresponds to the dilution producing less than 50% lysis of the added red blood cells.

Thus, where the serum sample contains high levels of anti-SLO antibody, there will be neutralisation of the active SLO up to a high dilution of the serum and therefore no lysis of the red blood cells. Conversely, where the serum sample contains lower levels of antibodies to SLO, there will be neutralisation only at low dilutions of the sample and there will be extensive lysis of the red blood cells at high dilutions of the sample.

However, there are a number of problems with these assays. The assays are difficult, time-consuming and require laboratory facilities. They utilise active SLO and, as stated, this protein is toxic and cytolytic and therefore laboratory facilities and trained personnel are required. The preparation of purified SLO from *S. pyogenes* is difficult and costly, particularly as SLO is sensitive to degradation by proteases produced by the *S. pyogenes*.

The present assays for detecting anti-SLO antibodies also use impure preparations of SLO which are unstable in liquid form. Thus, the SLO preparations are supplied as lyophilized powder in vials, each vial containing sufficient material for a set number of serum tests. Before use, the lyophilized powder must be reconstituted in a suitable solvent. However, the reconstituted SLO rapidly loses its activity, probably owing to the presence of contaminating proteases, and therefore it must either be used within a short time or discarded. Thus, it is costly to test individual serum samples as soon as they arrive in the laboratory. To overcome this problem laboratories generally store the samples until they have a sufficient number to enable economic use of a vial of lyophilized SLO. This means that there may be up to one weeks delay between taking the serum sample and obtaining the test result.

SUMMARY OF THE INVENTION

The present invention seeks to overcome these problems by providing a rapid and simple assay for anti-SLO antibodies in human serum, that can be performed in the absence of laboratory facilities. The assay can also be carried out immediately upon obtaining the serum sample. In addition the test does not rely on assaying lysis of test red blood cells to detect presence or absence of anti-SLO antibodies. The present invention does this by providing a non-toxic and non-cytolytic derivative of SLO that contains at least one epitope, preferably an immunodominant epitope (i.e. an antigenic site which elicits high levels of antibodies and/or antibodies which have high affinity for the epitope, and/or which will easily be detected by antibodies in sera samples). Such derivatives can conveniently be made using recombinant technology. The SLO derivative of the present invention is preferably also resistant to proteolytic degradation.

BRIEF DESCRIPTION OF THE DRAWING

FIG. 1 shows the nucleotide sequence of the N-SLO gene fusion in pMK306.

DETAILED DESCRIPTION OF THE INVENTION

The SLO gene has been cloned in *Escherichia coli* (hereafter called *E.coli*) by taking the SLO gene from *S.pyogenes* DNA, inserting it into suitable vectors that can be replicated in *E.coli* and transforming *E.coli* with the recombinant replicons. Transformed *E.coli* and its progeny containing the cloned SLO gene, express this gene and produce small quantities of active SLO. The complete nucleotide sequence of the cloned SLO gene has been determined and the amino acid sequence of SLO has been deduced from the determined DNA sequence. This data has been published by Kehoe and Timmis (1984, Infect. Immun. 43:804–810) and Kehoe et al (1987, Infect. Immun. 55:3228–3232).

From the amino acid sequence deduced from the complete nucleotide sequence of the cloned SLO gene, it can be inferred that the primary SLO gene product contains a short signal sequence at its N-terminal end which directs its secretion by the producing organism and that this signal sequence is removed during the export of SLO through the cytoplasmic membrane of *S.pyogenes* (to reach the culture supernatant) or by *E.*- coli expressing the cloned SLO gene (to reach the periplasm).

Two molecular weight forms of active SLO have been detected, (both in *S.pyogenes* culture supernatants and in the periplasm of *E.coli* expressing the cloned SLO gene), by sodium-dodecyl-sulphate polyacrylamide gel electrophoresis (SDS-PAGE). These are seen as a minor band (form I) with a relative molecular weight ($M_r$) of ca. 63,000 (originally estimated as ca. 69,000) and a more intense band (form II) with a $M_r$ of ca. 52,000 (originally estimated as ca. 60,000). It can be inferred that the low molecular weight form II is produced by proteolytic cleavage of the high molecular weight form I, after its secretion by the producing organism. There is evidence that the amino acid sequences removed by this proteolytic cleavage are from the N-terminal end of the form I SLO molecule.

One report in the literature describes three molecular weight forms of active SLO. Two of these correspond to the high and low molecular weight forms I and II described above and the third (form III) has a $M_r$ that is ca. 13,000 (corresponds to about 100 amino acids) smaller than the low molecular weight form II described above; this suggests that form III is about 200 amino acids smaller than the high molecular weight form I. It is not known if form III has lost additional amino acids from regions corresponding to the N-terminus or C-terminus (or both) of form II.

The data summarised above demonstrates that a significant proportion of SLO (i.e. at least ⅓ of the molecule) can be removed without destroying its cytolytic toxicity. Furthermore, there are a number of cytolytic toxins, including the toxin SLS produced by *S.pyogenes*, which are peptides consisting of a relatively small number (less than 50) of amino acids. Therefore it has been established that even short peptides can be cytolytic and toxic.

Therefore, the present inventor has proposed the solution of producing a derivative of the SLO protein which had lost its cytolytic toxicity, but which retained at least one epitope. It was not at all clear from the outset that this would be possible, but the present invention demonstrates that it is indeed possible and provides clear directions for producing suitable derivatives.

In one aspect the present invention provides a non-toxic and non-cytolytic derivative of streptolysin O (SLO) comprising at least one epitope characteristic of wild-type SLO.

Preferably, the SLO protein has been subjected to derivatisation within the region N-terminal of aa 383 of the complete SLO sequence reported by Kehoe et al (1987), supra. Suitably, the derivatisation involves altering the amino acid sequence by means of amino acid substitution, deletion, inversion, insertion or addition. Preferably, said epitope lies within the region aa 383–571 of the complete SLO protein sequence as reported.

Apart from derivatising the region responsible for cytotoxicity, the amino acid sequence of SLO depicted in FIG. 1 may be varied in other regions, for example by amino acid addition, deletion, substitution, insertion or inversion, so long as at least one epitope of SLO is retained. Such variants may be produced synthetically by mutation or in vitro DNA manipulation, or they may arise from natural allelic variation. The SLO amino acid sequence may be fused to exogenous amino acids, such as the lambda protein fragment described herein.

In another aspect, the present invention provides a DNA sequence encoding a non-toxic non-cytolytic derivative of streptolysin O as described above. The present invention also provides recombinant cloning vectors comprising such DNA sequences, recombinant expression vectors for producing the protein in a suitable transformed host, and such transformed host cells, especially an *E.coli* strain.

The present invention further provides a process which comprises, expressing a non-toxic and non-cytolytic protein derivative of streptolysin O by culturing such a transformed host cell so as to express the protein, and recovering the protein therefrom. In such a process the host cell may be *E.coli*.

The present invention also provides methods and diagnostic kits for detecting the presence or absence of antibodies to SLO in clinical samples, wherein the method comprises use of a non-toxic, non-cytolytic derivative of streptolysin O as described above. A typical diagnostic method may comprise contacting a clinical sample with the SLO derivative hereof immobilised on a suitable support, and then detecting any bound SLO antibody, for example by labelled anti-(human)antibody.

A further aspect of the invention comprises using the SLO derivative hereof to purify anti-SLO antibodies, animal or human, by immunoaffinity. This could be part of a process for producing monoclonal antibodies to SLO. The derivative could also be used as an immunogen to raise antibodies against SLO, either producing a polyclonal antiserum or in the production of monoclonal antibodies.

In order that the present invention may be more readily understood, preferred embodiments will now be described.

A DNA fragment containing the cloned SLO gene was generated by digestion of the recombinant plasmid pMK157 with the restriction endonuclease FspI and was cloned into the SmaI site of the vector plasmid pUC18. This produced a new recombinant plasmid, called pMK206, which expresses active SLO at low levels in *E.coli*. The structures of the parent plasmids, pMK157 and pUC18 have been described in the literature (Kehoe and Timmis, Supra. and Yanisch-Perron et al, 1985, Gene 33:103–119).

Plasmid pMK206 contains a single EcoRI site, located close to the 5' end of the SLO gene and single HpaI and EcoRV sites located within the SLO gene sequences. Plasmid pMK206 was digested with both EcoRI and HpaI and the larger of the two DNA fragments generated by this digestion was ligated to an EcoRI-HpaI DNA fragment from bacteriophage lambda that contains the $P_L$ promoter and part of the N gene sequences. This produces a recombinant DNA replicon, called pMK306, containing the 5' end of the lambda N gene fused in frame to about ⅔ of the SLO gene sequences. The nucleotide sequence of the N-SLO gene fusion in pMK306 is shown in FIG. 1 below. There, the sequences derived from the SLO gene commence at nucleotide 100. Nucleotides 1–99 encode 33 N-terminal amino acids from the lambda N protein, and nucleotides 100 and beyond encode amino acids 234 to 571 of the complete SLO protein, as reported. An *E.coli* strain expressing a temperature-sensitive lambda cI repressor was transformed with the resulting recombinant molecule.

When heat induced, cultures originating from the transformed strain express a non-cytolytic product containing the C-terminal $\frac{2}{3}$ (approx.) of SLO fused to 33 N-terminal amino acids from the lambda N protein. This product is expressed at high levels (greater than 0.5% of total cell protein) and reacts well with antibodies in a horse polyclonal anti-SLO serum. However the product was found to be sensitive to degradation in *E.coli* giving rise to low molecular weight breakdown products. This showed that the C-terminal $\frac{2}{3}$ of SLO contains a site or sites that are sensitive to degradation and that consequently should be avoided in the desired antigen. The sizes of the degraded products indicated that the location of the degradation-sensitive site or sites correspond to the central region of the SLO amino acid sequence. It was concluded that a derivative of pMK306 where the DNA encoding these degradation sensitive site or sites has been deleted might express a stable N-SLO fusion product, although it was not known whether the antigenicity would be retained.

A new recombinant plasmid, called pMK307, was constructed by deleting the small DNA fragment of pMK306 that is generated by digestion with HpaI and EcoRV. With reference to FIG. 1 the deleted sequences comprise nucleotides 100 to 546. *E.coli* containing a temperature-sensitive lambda cI repressor was transformed with this plasmid. Upon heat induction, cultures orginating from the transformants strain express a stable N-SLO fusion product consisting of the 33 N-terminal amino acids of the lambda N protein fused to the C-terminal $\frac{1}{3}$ (approx.) of SLO.

FIG. 1 also shows the deduced amino acid sequences for the SLO nucleotide coding insertions in plasmids pMK306 and pMK307. This product is non-cytolytic and is expressed at high levels in *E.coli.* On lysing these producing cells, it was found that most of the N-SLO fusion product obtained is insoluble. A purification protocol was devised that allows this product to be purified in a form that could be used to detect anti-SLO antibodies.

The pMK307 encoded N-SLO fusion product was purified in the following manner:

(i) *E.coli* expressing a temperature-sensitive lambda cI repressor and containing pMK307, was grown at 30° C. with aeration, and log phase cultures were heat-induced to inactivate the cI repressor, followed by incubation at 37° C. for a further two hours;

(ii) The cells were recovered by centrifugation, washed with buffer I (25 mM Tris-HCl, pH 8.0, containing 10 mM NaCl and 1 mM EDTA) and the washed cells were then lysed;

(iii) The lysate was centrifuged at 10,000×g for 10 minutes and the pellet was recovered, solubilised in buffer I containing 8M urea and the antigen was then purified further by ion-exchange chromatography;

(iv) Fractions from chromatography columns containing the product were identified by gel electrophoresis and pooled; and (v) Pooled fractions were disalysed against buffer I and any insoluble material in the dialysed fractions was solubilised by adding SDS to a final concentration of 0.1% (w/v).

The purified product was demonstrated to be non-cytolytic in vitro by hemolytic titration assays (such as the prior art assay described earlier), and non-toxic in vivo by intravenous immunization of laboratory mice.

The purified fusion product was tested for its ability to detect anti-SLO antibodies in serum by immobilising various quantities of the purified product on defined areas of filters with the aid of a Dot-Blot apparatus. The solid support carrying the antigen is then immunoblotted, using standard procedures. In this immunoblotting test serum at suitable dilutions are used as the primary antibody. After washing to remove any unbound antibody, the presence of bound antibody can be detected by standard antibody detection systems. The purified product was found to detect anti-SLO antibodies in human sera in a sensitive, specific and quantifiable manner and the results obtained were comparable to those obtained when the same sera were assayed by the standard assay described.

The present invention has thus disclosed for the first time that the cytolytic and toxic activity of SLO is separate from at least one of its suitable epitopes. It has disclosed a region in which such an epitope exists (aa 183–371 as depicted in FIG. 1, which corresponds to aa 383–571 of the complete sequence (Kehoe et al, 1987 supra)), and that cytolytic and toxic activity seem to require the presence of a sequence N-terminal of aa 234 of the complete sequence. However, it is possible that other suitable epitopes may exist in the region N-terminal of aa 234–382 of the complete SLO sequence, or even N-terminal of aa 234, which are still separate from the cytolytic and cytotoxic activity. Those skilled in the art can thus, if they so wish, identify by routine experimentation any further such epitopes from the region N-terminal of aa 234 of the complete sequence, and if found, they can be used in an exactly analogous manner to that indicated above. In its broad concept, therefore, the present invention provides a SLO derivative which retains an epitope while lacking its cytolytic and cytotoxic activity by virtue of its derivatisation. This derivatisation may for example be by way of deletion, insertion, inversion, addition, substitution etc., of the amino acid region N-terminal of aa 383.

Alternatively or additionally, the protein may be chemically derivatised to destroy the cytolytic and cytotoxic activity while retaining at least one suitable epitope.

I claim:

1. A non-toxic and non-cytolytic antigen derived from wild-type streptolysin O by deletion of amino acids and which includes the sequence of amino acids from 383 to 571 of the complete streptolysin O sequence and comprises at least one epitope reactive with anti-streptolysin O antibodies in human patient's sera and characteristic of wild-type streptolysin O and wherein the antigen is more resistant to proteolytic degradation than a fragment containing amino acids 234 to 571 of the complete streptolysin O sequence.

2. A method of purifying anti-streptolysin O antibodies which comprises binding them to a non-toxic and non-cytolytic antigen of claim 1.

3. A method of raising anti-streptolysin O antibodies which comprises immunizing a subject with a non-toxic and non-cytolytic antigen of claim 1.

4. A diagnostic kit for detecting the presence or absence of antibodies to streptolysin O in a clinical sample, which comprises a non-toxic and non-cytolytic antigen of claim 1 together with ancillary components for detecting the binding of the antigen to anti-streptolysin O antibodies in the sample.

* * * * *